(12) United States Patent
Hamer et al.

(10) Patent No.: US 6,677,474 B2
(45) Date of Patent: Jan. 13, 2004

(54) DIFUNCTIONAL IDBM AND RELATED COMPOUNDS AS NOVEL DENTIN BONDING AGENTS

(75) Inventors: Martin Hamer, Skokie, IL (US); Byoung In Suh, Oak Brook, IL (US); Amer Tiba, Schaumburg, IL (US)

(73) Assignee: Bisco, Inc., Schaumburg, IL (US)

( * ) Notice: Subject to any disclaimer, the term of this patent is extended or adjusted under 35 U.S.C. 154(b) by 94 days.

(21) Appl. No.: 10/071,644

(22) Filed: Feb. 7, 2002

(65) Prior Publication Data

US 2003/0180691 A1 Sep. 25, 2003

(51) Int. Cl.[7] ............................................... C07C 69/76
(52) U.S. Cl. ........................................... 560/57; 560/64
(58) Field of Search ...................................... 560/57, 64

(56) References Cited

U.S. PATENT DOCUMENTS

| | | | |
|---|---|---|---|
| 4,437,836 A | 3/1984 | Schmitz-Josten et al. | 433/199 |
| 4,439,380 A | 3/1984 | Michl et al. | 264/16 |
| 4,521,550 A | 6/1985 | Bowen | 523/116 |
| 4,816,495 A | 3/1989 | Blackwell et al. | 522/14 |
| 5,037,638 A | 8/1991 | Hamer et al. | 424/52 |
| 5,348,988 A | 9/1994 | Suh et al. | 523/118 |

*Primary Examiner*—Paul J. Killos
(74) *Attorney, Agent, or Firm*—Howrey Simon Arnold & White LLP

(57) ABSTRACT

Novel unsaturated esters for use in dentistry as bonding agents are produced by a reaction of a cyclic dianhydride with unsaturated alcohols. The novel unsaturated ester products have the formula:

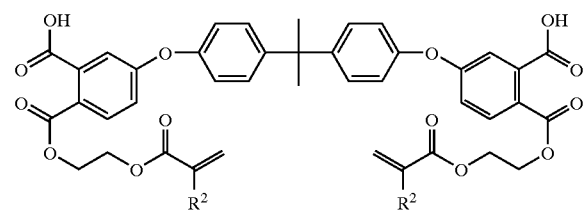

wherein $R^2$ is H or $CH_3$.

8 Claims, No Drawings

DIFUNCTIONAL IDBM AND RELATED COMPOUNDS AS NOVEL DENTIN BONDING AGENTS

BACKGROUND OF THE INVENTION

The present invention relates generally to a group of novel dimethacrylate compounds which can be used alone or in conjunction with other compounds, and which are useful as components in bonding systems for dental use, and to bonding systems incorporating such components which have superior adhesion to a variety of dental substrates.

BRIEF SUMMARY OF THE INVENTION

In accordance with the invention, there is provided a group of novel dimethacrylate compounds produced by the reaction of unsaturated alcohols with 4,4'-(4,4'-isopropylidenediphenoxy)bis(phthalic anhydride), also known as bisphenol A dianhydride. Bisphenol A dianhydride has the following structural formula:

(I)

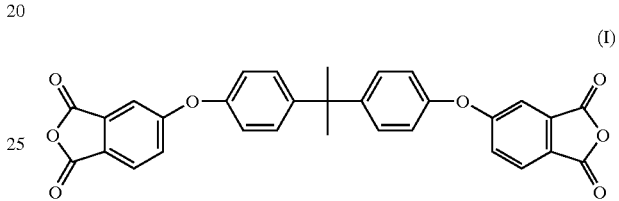

The unsaturated alcohols useful in the invention are those having the formula:

(II)

wherein $R^1$ is H, $CH_3$, or $=CH_2$; $R^2$ is H or $CH_3$; n is 1, 2, 3, or 4; and x is 0 or 1.

The reaction product produced in this manner is used in accordance with the invention in conjunction with other compounds such as a dentin conditioner or other components of a dental composite material. These materials are applied in solution to an area in which a bond is desired. The bond is usually completed by use with a self-curing initiator or a light cure system.

DETAILED DESCRIPTION OF THE INVENTION

The difunctional compounds of the present invention are, in general, symmetrical compounds having a polyaromatic nucleus substituted with two acrylate groups. Representative of the difunctional compounds of the present invention are those having the following structure:

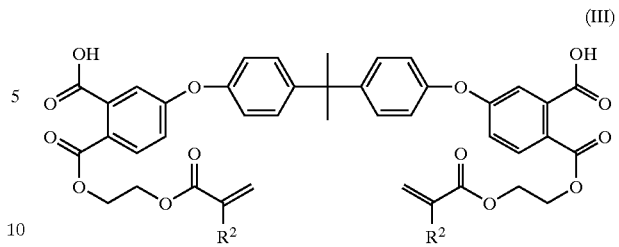

(III)

wherein $R^2$ is H or $CH_3$.

The novel diacrylate compounds are produced by a reaction of unsaturated alcohols with a cyclic dianhydride which has the following structure:

(I)

This cyclic dianhydride compound is produced by General Electric Co. under the name bisphenol A dianhydride and may be purchased from the Aldrich Chemical Co. under the name of 4,4'-(4,4'-isopropylidenediphenoxy)bis(phthalic anhydride). For producing the novel bonding agent components in accordance with the invention, the cyclic dianhydride as described above is permitted to react in the presence of a small amount of a tertiary amine such as triethylamine, with preferably at least two molar equivalents of an unsaturated alcohol having the formula II.

The preferred unsaturated alcohols used in making the components of the invention are hydroxyethyl methacrylate and hydroxypropyl methacrylate. When these alcohols are reacted with suitable anhydrides in accordance with the invention, there is produced a group of preferred compounds having the formula:

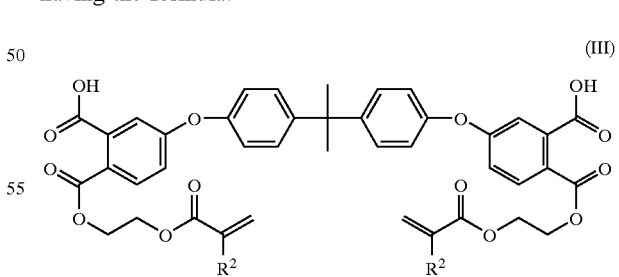

(III)

wherein $R^2$ is H or $CH_3$.

An example of the preparation of an unsaturated alcohol-cyclic dianhydride product is given in the following reaction, in which symmetrical dianhydride (I) is reacted with two moles of hydroxyethyl methacrylate.

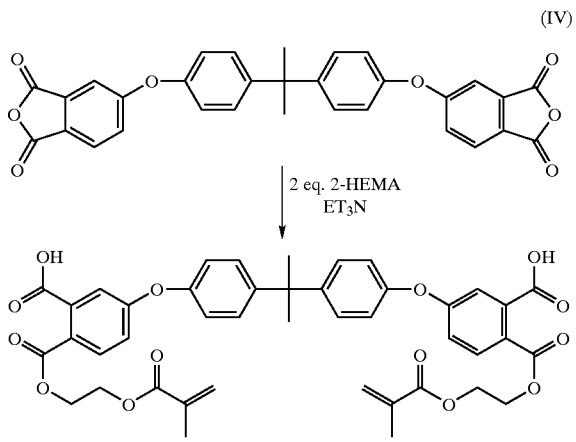

(IV)

The difunctional product, 4,4'-(4,4'-isopropylidenediphenoxy)bis(phthalate dimethacrylate ester) (IDBM, III) illustrated in the above reaction and its analogs may be one component of a novel dental bonding composition in accordance with the invention. The novel dental bonding compositions of the present invention and methods for their use have particular application in the field of restorative dentistry.

A preferred bonding system comprises (a) a dentin conditioner which is the reaction product of a cyclic acid anhydride having 3–12 carbon atoms with an ethylenically unsaturated alcohol having 3–12 carbon atoms, as disclosed in our U.S. patent application Ser. No. 07/471,882, now abandoned, and (b) a two-part dentin primer, the first part of which comprises the reaction product of an N-arylglycine with glycidyl methacrylate, having the formula:

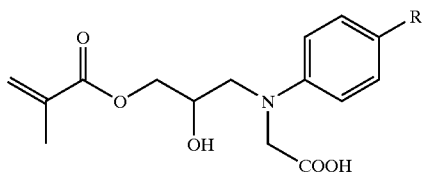

wherein R is hydrogen or H or $CH_3$.

When R is $CH_3$, the reaction product (V) is designated as NTG-GMA, and when R is H, as NPG-GMA. The second part of the two-part primer is selected from products, such as IDBM or its analogs disclosed afore.

Other preferred compositions according to the present invention comprise a difunctional compound (III), a filler portion, a polymerization catalyst portion comprising a polymerization compound or system. Optionally, the compositions may also include an additional multifunctional and/or monofunctional comonomer portion, antimicrobial agents, opaquifiers, fluoride-release agents, colorants and other components, which impart desirable properties to the composition. Such additional agents may be incorporated into one or more of the monomer, comonomer or filler portions of the compositions, or may be added in small amounts to the composition during formulation. Difunctional compounds (III) are used to build up a better cross-linking structure in the polymer matrix. This structure plays a very important role in the mechanical properties of the dental materials.

Presently preferred amounts of difunctional compound (III) in compositions of the present invention are from about 5 to about 35 weight percent of the total composition. Presently more preferred amounts are in the range of about 10 to about 25 weight percent of the composition.

Preferred fillers according to the present invention include one or more well-known sub-micron size fillers. For example, sub-micron size fillers are silanated oxides of aluminum, zirconium and silicon, silicate glasses, and barium or strontium glasses. The use of sub-micron size fillers is presently preferred to minimize surface wear and "plucking" of filler components from the restorative surface, as well as imparting a surface which may be easily polished by the dental professional. Preferred contemplated filler particles have an average size of about 0.04 to about 40 microns. Presently more preferred fillers have an average particle size of about 0.05 to about 10 microns.

The filler portion may also include caries inhibiting agents such as slow releasing fluoride agents to help inhibit caries from forming in the adjacent tooth structure. For example, glass ionomer 1X 1944 from Ferro Corporation, Cleveland, Ohio, which contains such a slow release fluoride agent, is expected to have utility in the present invention.

The filler or fillers are present at about 75 to about 95 weight percent of the contemplated compositions of the present invention, and are more preferably present at about 80 to about 90 weight percent of the composition. The amount of the filler component is adjusted in view of the other components of the composition and in view of the intended use of the composition, it being well known in the art that higher filler amounts generally impart higher compressive strengths to a composition, but also tend to increase viscosity and decrease flowability of the composition. Presently preferred fillers include silanized barium glass from Ferro Corporation, Cleveland, Ohio, silanized submicron glasses such as OX-50 or Aerosil R972 from DeGussa, Richfield Park, N.J., and porcelain ground (SR) glass such as (RWG) from Ferro Corporation, Cleveland, Ohio.

Optionally, the filler portion is formulated to include appropriate coloring agents in varying amounts to provide the dental professional with a range of colors in the composition, which may be selected for compatibility with the shade of the patient's tooth undergoing restoration. Such coloring or tint agents are well known in the art, and may be included in small amount of about 1 weight percent or less of the total composition. Such fillers can also be selected to be radioopaque. For example, appropriate amounts of radioopaque barium, strontium or zirconium glass may be used as all or part of the filler portion, which can assist the dental professional in his or her post-treatment examination of the patient.

A polymerization catalyst compound, composition or system is also included in the preferred compositions of the present invention. Such polymerization compounds compositions or systems (hereinafter referred to as "systems") are well known in the art.

They generally fall within one of three categories: (1) self-curing chemical systems, which initiate polymerization upon admixing two or more compounds; (2) light-initiated polymerization systems; and (3) heat-initiated polymerization systems. A polymerization system employing two or more initiators, i.e. light/self cure or light/heat initiated systems is also contemplated to give the dental professional additional flexibility in the restorative procedures.

Exemplary self-curing systems include traditional free radical polymerization initiators normally used with polymerizable ethylenically unsaturated materials and resins. For example, organic peroxide initiators and amine accelerations such as those disclosed in U.S. Pat. No. 4,816,495, whose disclosure is hereby incorporated by reference, may be used, and, as taught therein, packaged separately from the polymerizable monomer components of the system and admixed with the monomers shortly before application to the tooth or dental appliance.

A light or photo-curing or photosensitive polymerization initiation and curing system is also included in a contemplated light-curable composition of the present invention. A contemplated photo-curing system is activated to harden and cure the composition by irradiation with visible or UV light. For example, visible light of a wavelength of about 400 to about 500 μm initiates rapid and efficient curing.

A light or photo-curing or photosensitive polymerization initiation and curing system according to preferred embodiments of the present invention include alpha-diketone light-sensitive initiator compounds such as benzophenone or a derivative, or an a-diketone such as benzyl or Camphorquinone (CQ) and CQ derivatives and certain tertiary aromatic amine polymerization accelerator compounds. Preferably, photo-initiator systems according to the invention are sensitive to visible light and possibly into a range of other wavelength light that is not harmful to a patient undergoing a dental procedure. Some compounds that may be suitable ultraviolet light-sensitive initiators are 1,2-diketones, benzophenones, substituted benzophenones, benzoin methyl ether, isopropoxybenzoin, benzoin phenyl ether, and benzoin isobutyl ether. Camphorquinone or a CQ derivative is presently preferred.

Presently preferred CQ or CQ derivatives may be added to the composition of the present invention in concentrations that range from about 0.01 wt. % to about 5 wt. %, more preferably from about 0.05 wt. % to about 2 wt. %, and presently most preferably from about 0.1 wt. % to about 1.0 wt. % of the total composition.

As mentioned above a tertiary amine reductant or its salt is also included. Exemplary tertiary amines include tributylamine, tripropylamine, N-alkyldialkanol amines such as N-methyldiethanolamine, N-propyldiethanolamine, N-ethyldiisopropanolamine and trialkanolamines such as triethanolamine and triisopropanolamine. Further useful tertiary amines are specifically disclosed in U.S. Pat. Nos. 4,439,380; 4,437,836; and 4,816,495. Ethyl 4-dimethylamino benzoate (EDMAB) is a presently preferred tertiary amine reductant.

Presently preferred concentrations of tertiary aromatic amine compounds of the present invention of the formula identified above are from about 0.01 wt. % to about 10 wt. %, more preferably from about 0.05 wt. % to about 5 wt. % and presently most preferably from about 0.1 wt. % to about 2 wt. % of the total composition. The amount of each component of the photo-initiator system depends in part on the amount of monomer present in the solution whose polymerization is to be catalyzed. Particularly preferred photo-initiator systems include CQ and ethyl 4-dimethylaminobenzoate (EDMAB).

The photo-curing system is present in an amount sufficient to cure the cement to a desired strength preferably within about two minutes upon irradiation with light as above. More preferably, the cure time is less than about one minute, and most preferably about 20 to about 30 seconds. In usual practice, both components of the photo-curing system constitute less than about two percent of the weight of the dental compositions of the present invention, and more preferably less than about 1 weight percent.

Heat-initiated polymerization systems are also contemplated in the compositions of the present invention. Preferred heat initiators will initiate curing at around 60 to 150 degrees Centigrade, and more preferably about 100 to 130 degrees Centigrade. Such systems include benzoyl peroxide, t-butyl perbenzoate, 1,1-di(tert-butyl)peroxide and other well-known catalysts capable of initiating polymerization of ethylenically unsaturated groups or resins.

As indicated above, it is also contemplated that the polymerization initiator system of the present invention may include two or more initiators in the composition. For example, a combination of a light cure initiator system utilizing CQ alone or in combination with a tertiary amine reductant along with a heat curing agent such as t-butyl perbenzoate is expected to have utility in the present invention. Such multi-initiator systems may have utility in that they may include both a rapid cure initiator (light or heat cure) to impart significant polymerization in the dental office or dental laboratory. For example, a light cure system in combination with a longer time self-cure initiator, which continues to cause further polymerization after the patient leaves the office and further secures the restorative to the tooth structure, is also contemplated.

Such dual cure light/heat systems, as well as their respective single initiator systems, are also desirable in that they may be formulated and packaged in one container or syringe, thereby avoiding the need for mixing by the dental professional before application. For example, as set out in the following examples, such one-component systems exhibit good shelf life of more than a year when stored away from light at room temperature. If self-curing compositions are desired, the self-curing initiator may be packaged in one of two containers separately from the polymerizable components of the composition, with the contents of both containers being admixed shortly before use in the dental office.

In general, a highly loaded composite looks very dry and is very hard to handle. Compositions of the present invention also include suitable monomer(s) containing one or more functional groups capable of polymerization reaction with difunctional compound (III). The monofunctional comonomer acts as a diluent to control or reduce the viscosity of the resin as well as to provide fewer polymerization sites, both of which assist in formulating the composition. The addition of a viscosity controlling monofunctional monomer makes the composition and composites of the present invention as easy to work with as normal hybrid composites. Multifunctional, comonomer(s) are selected such that they contain two functional groups, which are capable of undergoing polymerization reactions with the other monomer(s) to help impart good flexure and tensile strength to the composition as well as a relatively high degree of cross-linking throughout the composition. Such monofunctional and multifunctional comonomer(s) are preferably present in amount of from about 2 to about 10 weight percent of the composition. The amount of the comonomer portion in the overall composition is dependent in part on the amount of filler and difunctional compound (III) in the composition and in part on the desired viscosity and flow characteristics of the composition.

Suitable monofunctional and multifunctional monomers may include well-known mono-, di-, tri-, and tetraacrylate and methacrylates such as 2,2-bis[4-(3-methacryloxy-2-hydroxypropoxy)phenyl]-propane (BISGMA), Bisphenol A dimethacrylate (Bis A Dima), ethoxylated Bis A Dima, neopentylglycol dimethacrylate, decanediol-1,10-dimethacrylate, dodecanediol- 1,12-dimethacrylate, 1,4-butanediol dimethacrylate, ethyleneglycol dimethacrylate, diethyleneglycol dimethacrylate, triethyleneglycol dimethacrylate (3EGDMA), tetraethyleneglycol dimethacrylate (4EGDMA), polyethyleneglycol dimethacrylate, propyleneglycol dimethacrylate, dipropyleneglycol dimethacrylate, tripropyleneglycol dimethacrylate, tetrapropyleneglycol dimethacrylate, polypropyleneglycol dimethacrylate, hexamethyleneglycol dimethacrylate (HMDA), 2,2-bis(4-methacryloxyphenyl)propane, 2,2-bis (4-methacryloxyethoxyphenyl)propane, 1,2-bis(3-methacryloxy-2-hydroxypropoxy)ethane, CPDM—the reaction product of cyclopentane tetracarboxylic acid dianhydride and 2 moles of hydroxyethyl methacrylate (HEMA), tetrahydrofurfuryl cyclohexene dimethacrylate (TCDM)—the reaction product of Epiclon B-4400 (Dainippon Inc. and Chemicals Inc., Ft. Lee, N.J.) with 2 moles of HEMA, 2,2-bis(4-methacryloxyphenyl)-propane, 2-hydroxy-1,3-dimethaeryloxypropane, di-2-methacryloxyethyl-2,2,4-trimethylhexamethylene dicarbamate (UDMA), di-2-methacryloxyethylisophorone dicarbamate, and di-2-methacryloxyethyl-2,4- or 2,6-tolylene dicarbamate.

Optionally, one or more of the monomer compounds may include a caries inhibiting agent that helps to prevent or inhibit caries formation in the adjacent tooth structure. For example, the fluoride release monomer disclosed in U.S. Pat. No. 5,037,638, whose disclosure is incorporated by reference, may have utility in the present invention as part of the monomer portion of the composition.

Still further ingredients such as pigments, tints, stabilizers, surfactants, fluoride release agents and thickening agents may be added to the composition to enhance its stability, color and beneficial properties. For example, well-known UV absorbers such as Uvinul® 3000 available from BASF Corp. can be present at less than about 0.5 weight percent, and polymerization inhibitors such as hydroquinone monomethyl ether (MEHQ) or 2,6-di-tert-butyl-4-methylphenol (BHT) that can be present at less than 0.1 weight percent, and more usually at less than 0.01 weight percent in the composition. Uvinul® 3000 is preferred as the light stabilizer and MEHQ is preferred as the polymerization inhibitor.

Preferred methods of use of the aforementioned compositions include their use as composite in classic dental restorative procedures such as Class V restorations. Such methods include the usual cleaning and preparation of the tooth surface, followed optionally and preferably by application of a dental adhesive composition, followed by application and curing of the dental compositions indicated above. For example, prepared restorative sites may be pre-treated with dental bonding adhesive systems such as "One Step", "ALL BOND 2" or "ALL-BOND 3" from Bisco, Inc., Schaumburg, Ill. according to the manufacturer's instructions. Compositions according to the present invention are then applied to the tooth, preferably by syringe in incremental layers of about 0.5 mm to about 2 mm and cured for about 20–40 seconds (depending on the shade of the composition, darker having higher application times), followed by additional layers and curing until the cavity is completely filled to the cavosurface margin. Any excess material is removed immediately from the surface and the restoration is finished and polished by conventional techniques such as diamonds, discs and polishing pastes. Such finishing also removes any oxygen-inhibited uncured or partially cured layer on the surface of the restoration, which if left in place, might cause staining of the surface over time.

It will also be appreciated by those skilled in the art that the dental compositions and the methods of the present invention have significant utility in other restorative applications. For example, compositions of the invention may also be used as liners in Class I, II or III restorations. In Class I and II restorations, which typically experience considerable occlusal forces from mastication, use of conventional inflexible, highly filled and hard composites has often led to problems such as creation of marginal gaps. Use of the compositions according to the present invention as liners under such conventional compositions permits their use and avoids such gaps.

Other areas of use of the present inventions which will occur to those of skill in the art include without limitation: use of the compositions under temporary crowns, so-called Class III type restorations, small non-stress Class IV repairs, porcelain veneer bonding, tunnel preparation, splinting, marginal defect repair, deciduous class I or II repair, impart seals, buccal pit restorations, porcelain repair, pit and fissure sealant, adult preventative resin, small core build-up applications, and where maximum strength and polishability is desired.

The following examples are given by way of illustration but without limitation. The preparation of the high molecular weight, multifunctional compounds of the present invention is illustrated in the following example 1. Example 2 describes preferred formulations of the invention. All parts and percentages are by weight unless otherwise noted. Compounds identified herein are compounds purchased from the manufacturers indicated in the following list, which list also includes the abbreviations used herein to identify those compounds.

| | |
|---|---|
| Acetone | (Ashland Chemical Inc.). |
| BisGMA | Bisglycidylmethacrylate (Bisco, Inc.). |
| CQ | Camphorquinone (Hampford Research, Inc., Stratford, Connecticut). |
| DMABA | Dimethylaminobenzoic acid (Aldrich Chemical Co., Milwaukee, Wisconsin). |
| EDMAB | Ethyl dimethylaminobenzoate (Aldrich Chemical Company, Milwaukee, Wisconsin). |
| ETOH | Ethanol (AAPER Alcohol & Chemical Co.). |
| 2-HEMA | 2-Hydroxyethyl methacrylate (Rohm & Haas Co.). |
| HPMA | Hydroxypropyl methacrylate (Rohm & Haas Co.). |
| Na NTG-GMA | Sodium-N-tolyl glycine-glycidylmethacrylate (Esschem). |

EXAMPLE 1

Preparation of IDBM Monomer (III)

4,4' (4,4'-Isopropylidenediphenoxy)-bis(phthalic anhydride) (IBA), 67.75 g (0.13 mole), was ground and weighed into a 250 ml round bottomed flask fitted with a moisture trap, mechanical stirrer, and a thermometer. 2-Hydroxyethyl-methacrylate (HEMA), 61.0 g (0.364 mole) was added together with 2.5% triethylamine, 3.2 g (0.03 moles). The mixture was stirred and heated under nitrogen at 65° C. for six to eight hours, during which time a clear solution resulted. At this time, the infrared spectrum of the product, 4,4' (4,4'-Isopropylidenediphenoxy)-bis(phthalic) dimethacrylate (IDBM), revealed the disappearance of the anhydride absorption bands.

EXAMPLE 2

Preparation of Dental Compositions

Dental compositions were formulated according to the following amounts and procedures. Twenty (20) gram bonding-resin compositions were prepared containing the weight percent of each component as identified in the formulations in Table 1 below by weighing out in grams one-fifth of the indicated weight percent for that component.

The procedure for preparation of the composition consisted of three admixing steps.

First, 20.0–32.0% of the IDBM and 0.1% of the photo-initiator were combined in a 100 ml beaker in the appropriate weight (such that the total weight percentage was 100%) of acetone and mixed with a magnetic stir bar until all monomers dissolved (approximately one half hour). For all formulations, acetone was the solvent, and BisFil All-Purpose Composite was used as the restorative.

The mixture was protected from light during and after such mixing. The resultant resin compositions exhibited good viscosity and flowability and were easily dispensable from their syringes.

TABLE 1

| Formulation # | Wt. % IDBM | Wt. % CQ | Wt. % NaNTG GMA | Wt. % HEMA | Wt. % BisGMA |
|---|---|---|---|---|---|
| 1 | 0.500 | 0.006 | 0.030 | 0.130 | 0.340 |
| 2 | 0.500 | 0.001 | 0.030 | 0.130 | 0.340 |
| 3 | 0.200 | 0.006 | 0.030 | 0.150 | 0.620 |
| 4 | 0.200 | 0.006 | 0.060 | 0.050 | 0.690 |
| 5 | 0.200 | 0.004 | 0.030 | 0.054 | 0.716 |
| 6 | 0.200 | 0.001 | 0.060 | 0.150 | 0.590 |
| 7 | 0.325 | 0.006 | 0.060 | 0.150 | 0.465 |
| 8 | 0.500 | 0.001 | 0.060 | 0.050 | 0.390 |
| 9 | 0.500 | 0.006 | 0.060 | 0.050 | 0.390 |
| 10 | 0.352 | 0.006 | 0.030 | 0.050 | 0.568 |
| 11 | 0.450 | 0.001 | 0.060 | 0.150 | 0.340 |
| 12 | 0.340 | 0.004 | 0.030 | 0.150 | 0.480 |
| 13 | 0.500 | 0.004 | 0.045 | 0.083 | 0.373 |
| 14 | 0.500 | 0.001 | 0.030 | 0.050 | 0.420 |
| 15 | 0.300 | 0.001 | 0.030 | 0.102 | 0.668 |
| 16 | 0.300 | 0.001 | 0.060 | 0.050 | 0.690 |
| 17 | 0.300 | 0.001 | 0.045 | 0.150 | 0.605 |
| 18 | 0.345 | 0.001 | 0.043 | 0.095 | 0.518 |
| 19 | 0.200 | 0.004 | 0.060 | 0.100 | 0.640 |
| 20 | 0.465 | 0.006 | 0.045 | 0.150 | 0.340 |

TABLE 2

| Formulation # | SBS (Mpa) at 37° C. (Wet) | SBS (Mpa) at 37° C. (Dry) |
|---|---|---|
| 1 | 16.44 ± 2.62 | 15.83 ± 2.28 |
| 2 | 24.40 ± 1.77 | 22.26 ± 2.46 |
| 6 | 21.43 ± 2.51 | 19.87 ± 2.96 |
| 7 | 23.19 ± 1.55 | 21.95 ± 1.67 |
| 11 | 20.05 ± 2.04 | 21.15 ± 1.20 |
| 13 | 16.16 ± 1.92 | 20.50 ± 4.22 |
| 15 | 20.21 ± 3.75 | 19.58 ± 1.53 |
| 18 | 22.86 ± 2.79 | 21.04 ± 3.10 |
| 20 | 20.31 ± 3.22 | 21.61 ± 2.39 |

EXAMPLE 3

Testing of Dental Compositions

The compositions of Example 2 were tested to determine their wet and dry shear bond strength (SBS) on the indicated substrates according to the following methods.

a. Dentin Shear Bond Strength Test Procedure:

Five specimens of extracted human teeth were selected, embedded in resin discs, ground on the facial surface with a model trimmer to expose the dentin, and subsequently abraded with wet 600 grit SiC paper to create a flat and smooth dentin substrate for bonding. Each sample was then etched for 15 seconds using 32% phosphoric acid or 37% Uni-Etch, rinsed for 15 seconds with water, and placed in water at 37° C. The specimen was removed from the oven and placed tooth-side down on a moist Kimwipe®.

When ONE-STEP® (Bisco) Light-Cure Composite was used, 2 drops of bonding formulation were dispensed into a mixing well. Two consecutive coats of the bonding formulation were applied to the prepared, moist dentin surface of the tooth. The surface was air dried to evaporate solvent and the bonding formulation was photo-cured for 10 seconds using the above-identified lamp. Universal Bisfil was condensed into a #5 gelatin capsule post which was partially (⅔) filled with the cured same composite. The completely filled capsule was then placed directly on top of the prepared dentin or enamel/resin layer and excess composite was removed with a Hollenback carver while the post was held in place with gentle finger pressure. The post was photo-cured for 40 seconds on two sides using the above-identified lamp. The specimens were stored in DI water for 2 hours at 37° C. before being debonded in shear with a knife edge on an Instron model 1133 machine at a crosshead speed of 0.5 mm/min. Shear bond strength(s) was calculated in MPa by dividing the peak load by bonding area. The mean and standard deviations for bond strength were calculated from five replications for each formulation.

When ALL-BOND 2® (Bisco) Light-Cure Composite was used, 2 drops of each component were dispensed into a mixing well, mixed with a brush tip, and 5 consecutive coats of the bonding formulation were applied to the prepared, moist dentin surface of the tooth. The surface was air dried to evaporate solvent and additional coats were applied as needed to obtain the desired glossy surface. Once the desired surface was obtained, 1 drop of D/E resin was dispensed into a mixing well, mixed with a brush tip, and 1 coat of the bonding formulation was then placed, directly on top of the prepared dentin or enamel/resin layer on the tooth. Universal Bisfit was condensed into a #5 gelatin capsule post which was partially (⅔) filled with the cured same composite. The completely filled capsule was then placed directly on top of the prepared dentin or enamel/resin layer and excess composite was removed with a Hollenback carver while the post was held in place with gentle finger pressure. The post was photo-cured for 40 seconds on two sides using the above-identified lamp. The specimens were stored in DI water for 2 hours at 37° C. before being debonded in shear with a knife edge on an Instron model 1133 machine at a crosshead speed of 0.5 mm/min. Shear bond strength(s) was calculated in MPa by dividing the peak load by bonding area. The mean and standard deviations for bond strength were calculated from five replications for each formulation.

b. Enamel Shear Bond Test Procedure:

Adhesive shear bond strengths of self-etching primer/adhesive bonding-resin compositions to tooth enamel were determined by the procedure used for determining dentin shear bonding strengths set out above with the following modifications:

First, extracted teeth were imbedded to a lesser depth in the acrylic resin to permit better exposure of the enamel surface. Second, enamel surfaces were etched by application of two coats of the desired etching composition. Cure of the applied bonding composition(s), application and cure of composite and shear bond strengths were carried out according to the same procedures used for the dentin shear bond strength test procedures. The superior effectiveness of the formulations of the invention is also set forth Table 1 and in the following Table 3.

TABLE 3

Wet and Dry Bonding Dentin Shear Bond Strength (SBS) values of Formulation 18 using Example 2 protocols

| Specimen | Instron Reading(kg) | SBS (psi) | SBS (Mpa) | Notes |
|---|---|---|---|---|
| 1 wet | 38.7 | 3615.2 | 24.93 | |
| 2 wet | 39.7 | 3710.5 | 25.59 | |
| 3 wet | 31.9 | 2978.78 | 20.54 | |
| 4 wet | 31.6 | 2953.4 | 20.37 | |
| Average | 35.5 | 3314.4 | 22.86 | |
| St. Dev. | 4.3 | 404.3 | 2.79 | |
| Co. Var., % | 12.2 | 12.2 | 12.2 | |
| 1 dry | 25.5 | 2386.1 | 16.46 | Composite |
| 2 dry | 35.3 | 3299.3 | 22.75 | |
| 3 dry | 34.0 | 3178.7 | 21.92 | |
| 4 dry | 35.8 | 3341.3 | 23.04 | |
| Average | 32.6 | 3051.3 | 21.04 | |
| St. Dev. | 4.8 | 448.8 | 3.10 | |
| Co. Var., % | 14.7 | 14.7 | 14.7 | |

The data of Tables 1 and 2 illustrate the advantages of the bonding formulations of the present invention. Bonds made in accordance with the invention all produced bond strengths exceeding 16.0 NM/m$^2$.

It is expected that other commercial composites will also function well with applicants' bonding compositions and methods. The compositions using the bonding agents of the present invention exhibited good stability at room temperature for at least 6 months and at elevated temperatures for at least one month. It is also contemplated that the advantages inherent in applicants' bonding agents can be realized by formulating applicants' bonding agents in one or two parts and in placing those parts into kits containing one or two separate containers, the contents of which could be admixed by the dental professional in his or her office. Formulations of other stable bonding agent compositions according to the present invention will also be apparent to those skilled in the art in view of applicants' disclosure of their presently preferred compositions and presently preferred methods. The foregoing detailed description has been given for clearness of understanding only, and no unnecessary limitations should be understood therefrom, as modifications therefrom will be apparent to those skilled in the art.

What is claimed is:

1. A compound having the formula:

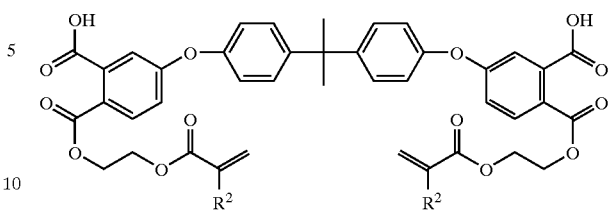

wherein $R^2$ is H or $CH_3$.

2. The compound of claim 1, wherein $R^2$ is $CH_3$.

3. A method of making a compound in accordance with claim 1, the method comprising
   contacting a cyclic dianhydride having the formula:

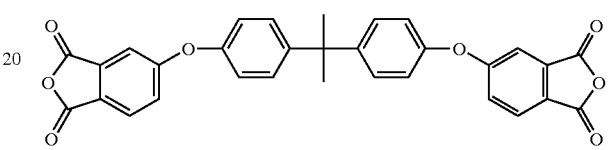

and an ethylenically unsaturated alcohol having 3 to 12 carbon atoms having the formula:

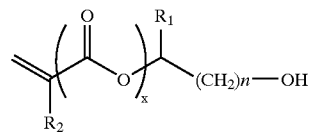

wherein $R^1$ is H, $CH_3$, or $=CH_2$; $R^2$ is H or $CH_3$; n is 1, 2, 3, or 4, and x is 0 or 1.

4. The method of claim 3, wherein the ethylenically unsaturated alcohol having 3 to 12 carbon atoms is 2-hydroxyethyl methacrylate.

5. A primer for improving the bond strength between a dental composite and dentin or a metal, said primer comprising the compound in accordance with claim 1.

6. A dental composite comprising the compound in accordance with claim 1.

7. A method for improving the bond strength between a dental composite and dentin or a metal which comprises applying to the surface of said dentin or said metal an effective quantity of a primer in accordance with claim 5 before the application of said dental composite thereto.

8. A kit for enhancing the adhesion of dental restorative materials and dental components to tooth dentin, tooth enamel and/or other dental substrates comprising a container containing a compound according to claim 1.

* * * * *